United States Patent
Abbott et al.

(10) Patent No.: US 8,841,640 B1
(45) Date of Patent: Sep. 23, 2014

(54) APPARATUS FOR INFECTION CONTROL

(71) Applicant: Inceptus Technologies, LLC, Sunnyvale, CA (US)

(72) Inventors: Ryan Abbott, San Jose, CA (US); Frederick Alexander Ginnebaugh, Sunnyvale, CA (US)

(*) Notice: Subject to any disclaimer, the term of this patent is extended or adjusted under 35 U.S.C. 154(b) by 0 days.

(21) Appl. No.: 13/798,090

(22) Filed: Mar. 13, 2013

(51) Int. Cl.
*A61N 5/06* (2006.01)
*A61L 9/20* (2006.01)
*A61M 16/04* (2006.01)

(52) U.S. Cl.
CPC .............. *A61L 9/20* (2013.01); *A63M 16/1055* (2013.01); *A61M 16/04* (2013.01)
USPC .................................................. 250/504 R

(58) Field of Classification Search
CPC ....... A61L 9/205; A61L 2/10; A61L 2202/24; A61L 9/20; A61L 2202/14; A61L 9/16; Y10S 28/909
USPC .................................................. 250/504 R
See application file for complete search history.

(56) References Cited

U.S. PATENT DOCUMENTS

| | | | |
|---|---|---|---|
| 4,653,493 A * | 3/1987 | Hoppough | 128/202.22 |
| 5,855,203 A * | 1/1999 | Matter | 128/207.14 |
| 6,470,888 B1 * | 10/2002 | Matter | 128/207.14 |
| 6,497,840 B1 | 12/2002 | Palestro et al. | |
| 7,258,120 B2 | 8/2007 | Melker | |
| 8,042,544 B2 | 10/2011 | Ward et al. | |
| 8,480,722 B2 * | 7/2013 | Klepper | 607/92 |
| 2004/0156908 A1 | 8/2004 | Polaschegg | |
| 2005/0271711 A1 | 12/2005 | Lynch et al. | |
| 2005/0274965 A1 | 12/2005 | Phillips et al. | |
| 2007/0083677 A1 | 4/2007 | Cecka et al. | |
| 2007/0102280 A1 * | 5/2007 | Hunter et al. | 204/157.15 |
| 2007/0207066 A1 * | 9/2007 | Thur et al. | 422/121 |
| 2008/0257355 A1 * | 10/2008 | Rao et al. | 128/207.14 |
| 2009/0004047 A1 * | 1/2009 | Hunter et al. | 422/4 |
| 2009/0038620 A1 | 2/2009 | Efrati | |
| 2010/0145252 A1 | 6/2010 | Polaschegg | |
| 2010/0168823 A1 * | 7/2010 | Strisower | 607/89 |
| 2011/0160643 A1 * | 6/2011 | Dacey et al. | 604/21 |

* cited by examiner

*Primary Examiner* — Michael Maskell

(57) ABSTRACT

A device that can sterilize material passing through it efficiently by utilizing an appropriate light source that can be powered by external sources (including use of an electromagnetic field to transmit energy) or by a power source that is contained within the device itself, which may include elements to create turbulence within the material passing through it, and elements to reflect the light source where useful but trap the light from escaping to ensure safety. The device may be rigid or flexible, possibly including a mechanism to fold or collapse the device for delivery through a port or lumen and expanded or unfolded prior to use.

20 Claims, 14 Drawing Sheets

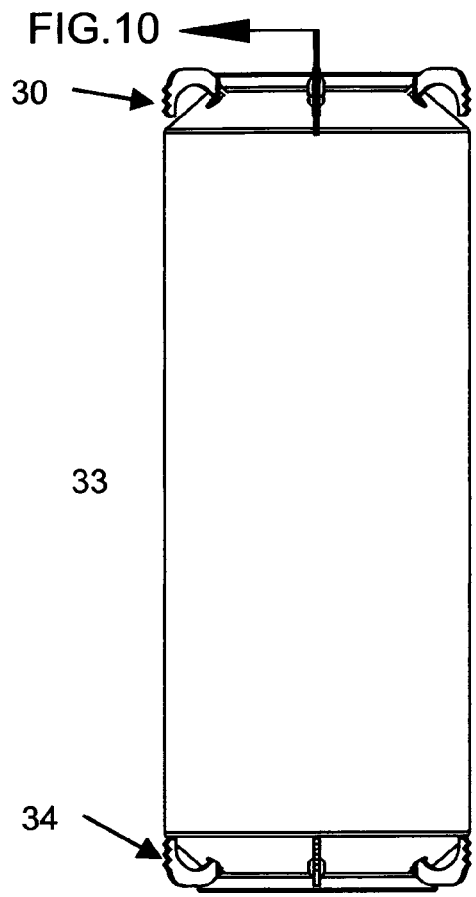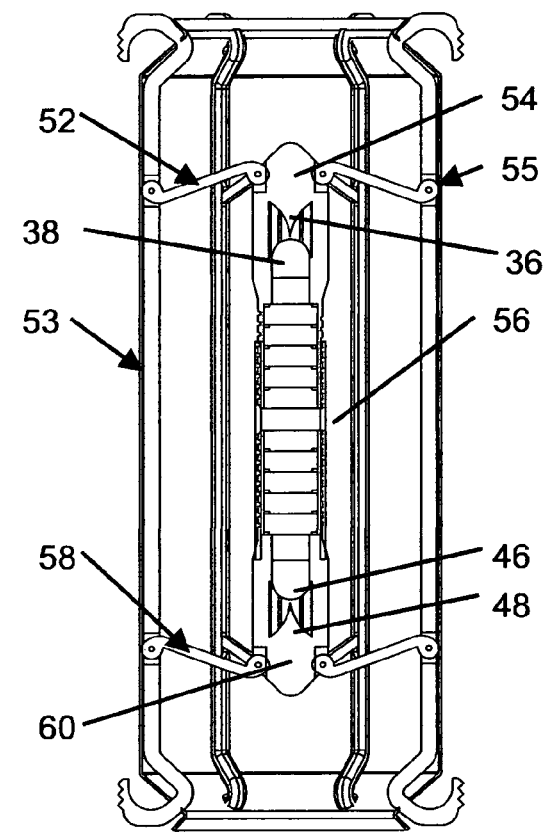
FIG. 9  FIG. 10

US 8,841,640 B1

APPARATUS FOR INFECTION CONTROL

FIELD OF THE INVENTION

Field of the invention relates to sterilization of a flowing fluid by method of novel placement of one or more light sources relative to the fluid and/or novel powering of light sources and/or use of turbulence and/or reflective surfaces to allow for use in a variety of environments, geometries, and applications.

BACKGROUND OF THE INVENTION

The need for infection control exists in many different situations and can be used to address many different needs. One of the apparent applications for infection control is in medicine. From device sterilization to drugs to address infection to topical application of infection fighting compounds to air handling to simple handwashing, much of medicine is focused on the need to provide infection control.

The need is particularly acute, for example in dealing with tuberculosis (TB), which as cited in U.S. Pat. No. 6,497,840 (8 Nov. 1993) by Palestro, et al, is the most common cause of infectious disease in the world today. It is believed that the infection rates are now increasing after a long period of decline in the US. Since TB transmission is primarily accomplished through suspension of microdroplets in the air, the need to manage that transmission is a significant element to reduce the rate of TB contraction. Prevention of the TB laden aerosols from entering the general environment through the use of masks to prevent cough or sneeze transmission is considered the standard of care. This is not completely effective however in that not all TB patients will be wearing a mask. It is inevitable that some TB laden aerosols will occur in the environment. In locations like hospitals, where there is a higher likelihood that individuals who have contracted TB will be present and already sick or compromised patients may be exposed, an additional line of defense against contracting TB is to also manage the aerosols themselves.

Of course, there are other infections that need to be addressed. Another prevalent example is the number of instances of pneumonia that are associated with ventilator use in hospitals. As described in U.S. Pat. No. 8,042,544 (2 Sep. 2005) by Ward et al., Ventilator associated pneumonia (VAP) is a potentially preventable cause of pneumonia that (ICU) and is associated with an increase in morbidity and mortality. It is estimated that cost of diagnosing and treating VAP exceeds 1.1 billion dollars annually (Young P J, Ridley S A, Ventilator-associated pneumonia, Diagnosis, pathogenesis and prevention, Anaesthesia 1999; 54(12):1183-97; Morehead R S, Pinto S J, Ventilator-associated pneumonia, Arch Intern Med 2000; 160(13): 1 926-36).

With this in mind, a device that could better address VAP, sterilize airborne TB, and be applicable in other arrangements would be extremely useful.

BRIEF SUMMARY OF THE INVENTION

Accordingly, an object of the invention is a device for sterilizing fluid flows. For a device of this type, the use of turbulence and reflectivity with an appropriate light source may allow for efficient microorganism destruction of material passing through a lumen and reduce device size, allowing for a variety of applications. The use of a flexible or folding device may allow for the navigation of tortuous paths for delivery and use of the device in areas that would otherwise not be feasible.

Another object of the invention may provide a device for implantation in a patient that sterilizes the inhaled and exhaled air of the patient.

Still another object of the invention may provide a respirator circuit capable of sterilizing the airflow, secretions, aspirated material and other fluids flowing from and to the patient.

Yet another object of the invention may provide a continuous fluid flow sterilization system for enclosed environments such as an automobile, aircraft, building or other system that would benefit from such an apparatus.

Additional objectives, advantages and novel features of the invention will be set forth in the description that follows and, in part, will become apparent to those skilled in the art upon examining or practicing the apparatus for infection control. The objects and advantages of the invention may be realized and obtained by the instrumentalities and combinations particularly pointed out in the appended claims.

One embodiment of the invention is an apparatus for in vivo sterilization of respiration. The device may be composed of a tubular structure which is collapsed for placement into the patient's trachea. Once placed, the structure may be expanded such that the respiration passes through the structure. The volume between the inlet and outlet may contain ultraviolet light sources, reflective surfaces, and turbulence inducing features, which cause the fluid to be exposed to the light from more directions and for longer times than would be possible otherwise. Fluid may be composed of air, blood, gastric contents, viruses in the air, bacteria in the air, secretions, viruses in the secretions, bacteria in the secretions, aspirated bacteria, aspirated viruses, aspirated biological material, other biological constituents, liquids, gases and other substances commonly known as fluids. The light sources may be powered by batteries within the tubular structure.

Another embodiment of the invention is an apparatus for in vivo sterilization of a respirator circuit. The device may be composed of a tubular structure which is composed of an inlet and outlet that reduces the emission of UV light out of the invention, referred to as a light trap, but allows fluid to flow through the invention. A light trap may be composed of any structure that reduces or prevents light from passing, escaping, or being transmitted. The device may be placed into the respirator tubing between the respirator machine and the patient. It may be placed in the balloon portion of the tracheal tube, at the end of the tracheal tube, or further within the tracheal tube so as to sterilize the airflow, aspirated material, and secretions. External o-rings may be present to assure that fluid flow passes through the lumen of the device. The volume between the inlet and outlet may contain ultraviolet light sources reflective surfaces, and turbulence inducing features, which cause the fluid to be exposed to the light from more directions and for longer times than would be possible otherwise. The light sources may be powered by electrical induction from a magnetic coil external to the device and respirator tubing or by other appropriate power sources.

Another embodiment of the invention may be that the invention serves as the inlet and outlet of a respirator mask. The device may be composed of a structure, with an inlet and outlet, that blocks the passage of light, but allows fluid flow. The volume between the inlet and outlet may contain ultraviolet light sources, reflective surfaces, and turbulence inducing features, which cause the fluid to be exposed to the light from more directions and for longer times than would be possible otherwise. The light sources may be powered by power sources external to the lumen.

BRIEF DESCRIPTION OF THE DRAWINGS

The accompanying drawings, incorporated in and forming part of the specification, illustrate several aspects of the apparatus for infection control and, together with their descriptions, serve to explain the principles of the apparatus for infection control. In the

DRAWINGS

Figure 1:
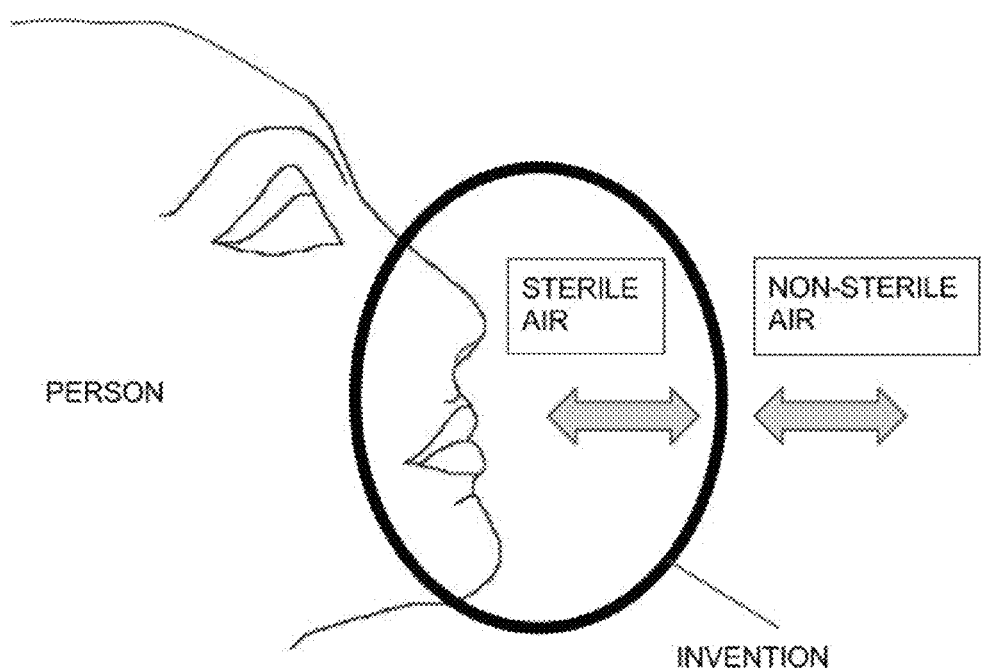

FIG. 1 depicts the schematic of how the invention may sterilize fluids flowing from and to the user, while still allowing airflow for respiration.

Figure 2:
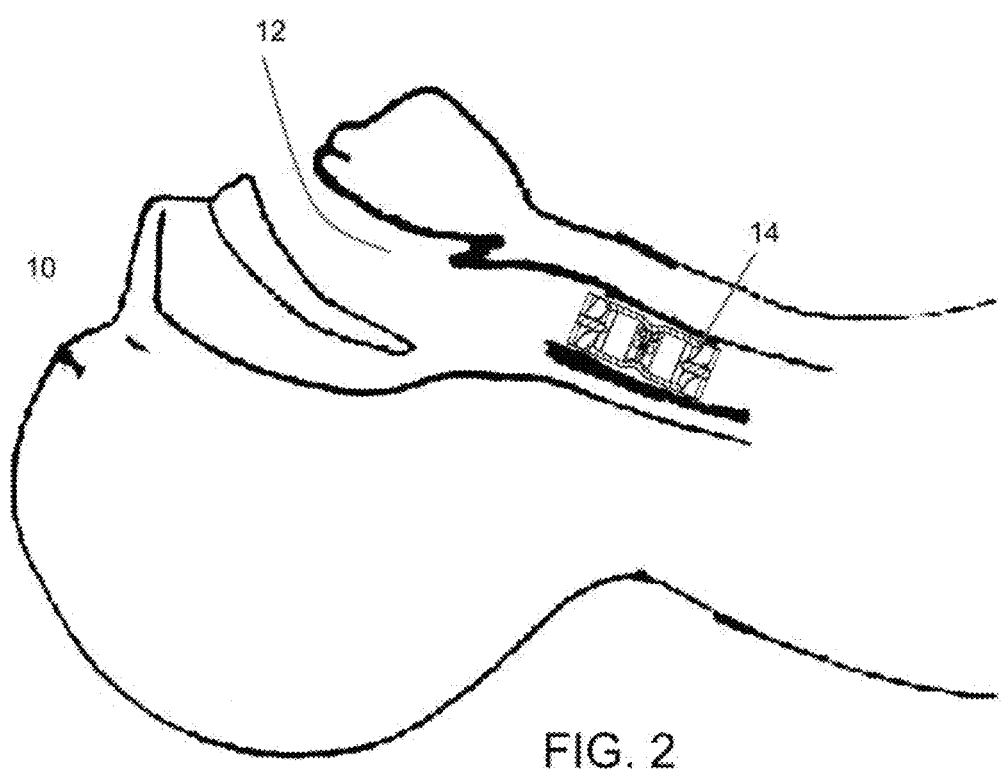

FIG. 2 depicts a schematic, cross sectional side view of an implanted embodiment of the invention may be capable of sterilizing respiration.

Figure 3:
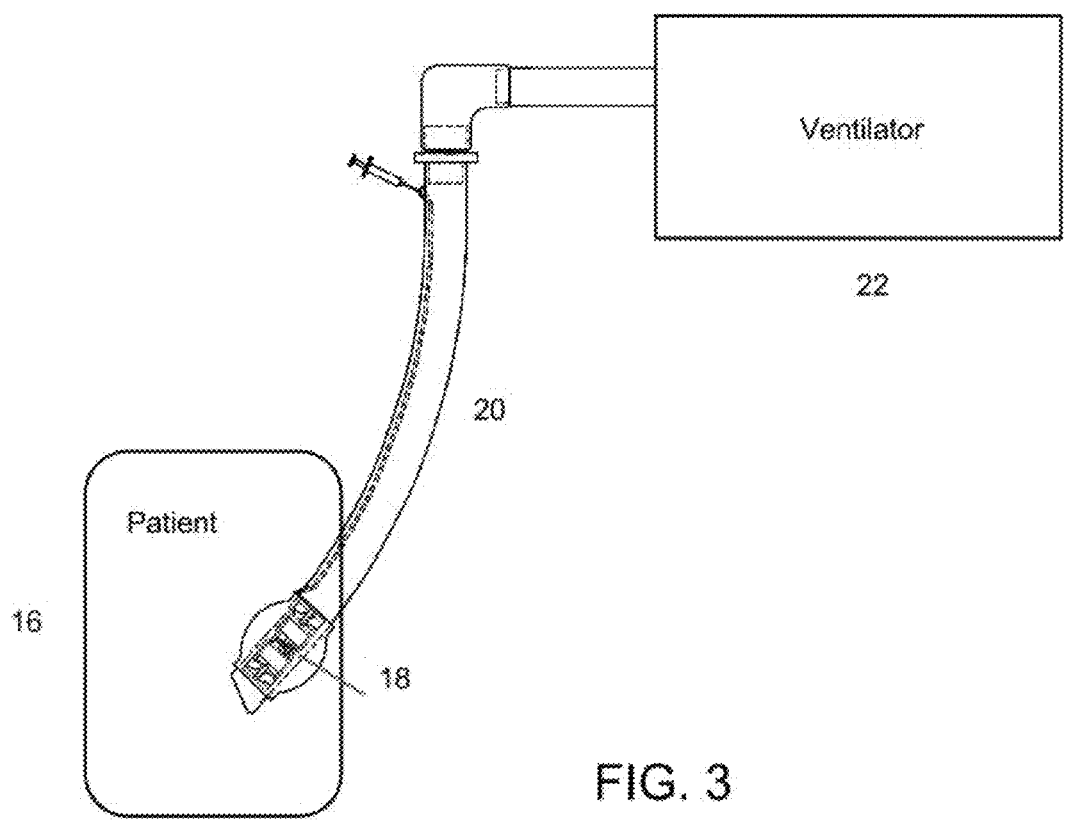

FIG. 3 depicts a schematic view of the invention in a respiratory system positioned at the balloon section of a tracheal tube that may be capable of sterilizing the inhalation, exhalation, secretions, and aspirated material of the patient.

Figure 4:
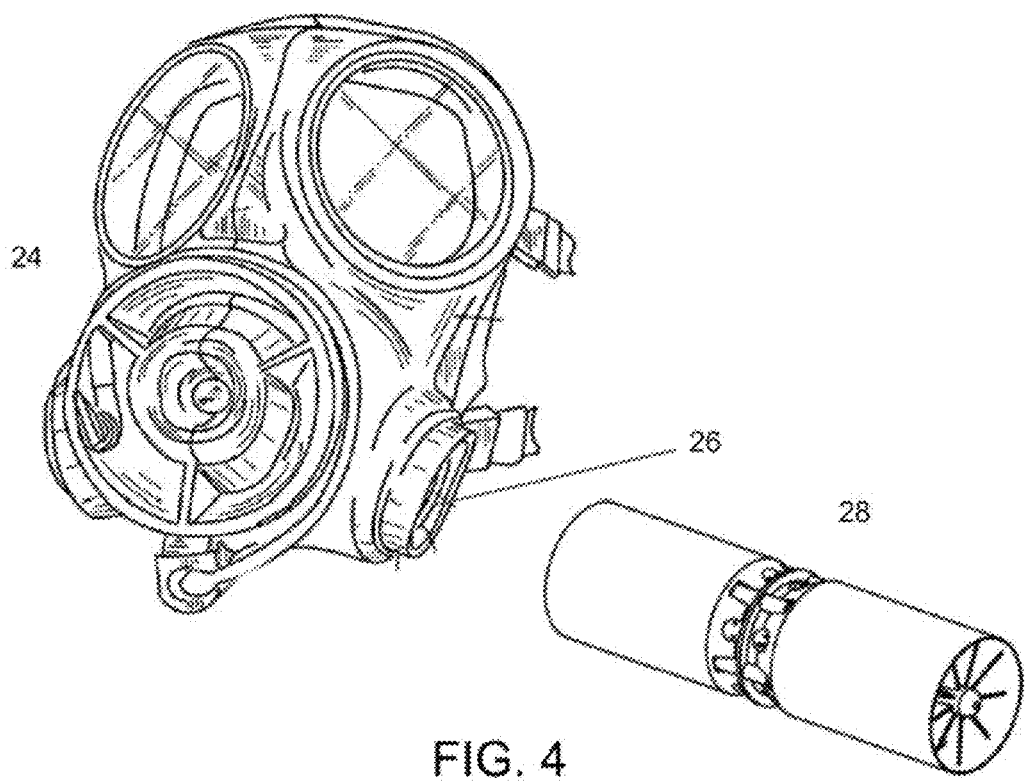

FIG. 4 depicts a schematic blow apart view of an embodiment of the invention in a mask that may be capable of portable sterilization of inhalation and exhalation of a person.

Figure 5:
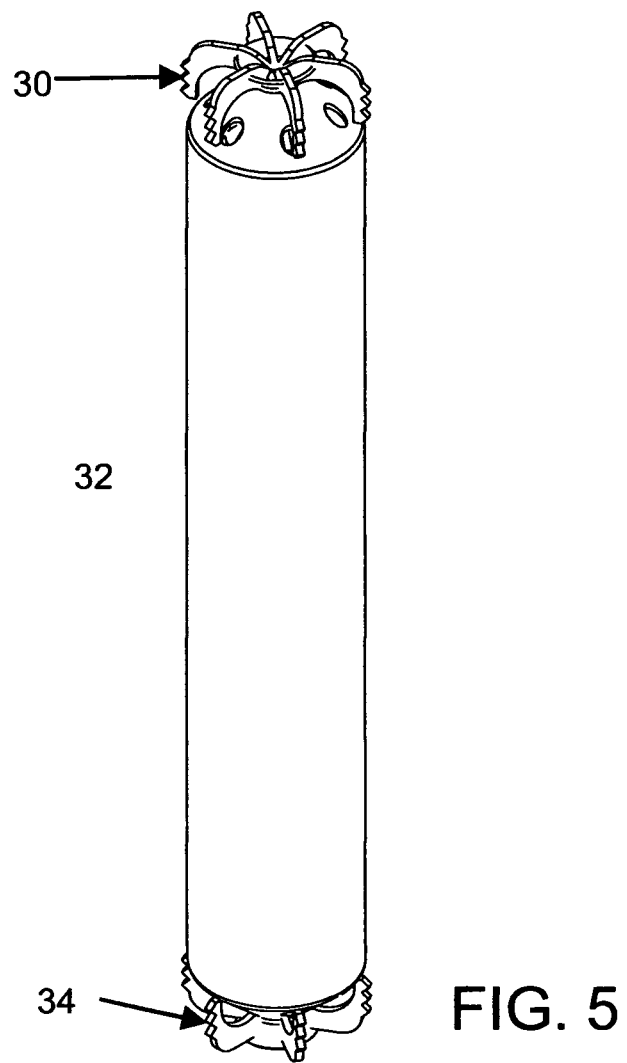

FIG. 5 depicts an off-axis exterior view of an implantable embodiment of the invention in a collapsed state.

Figures 6, 7:
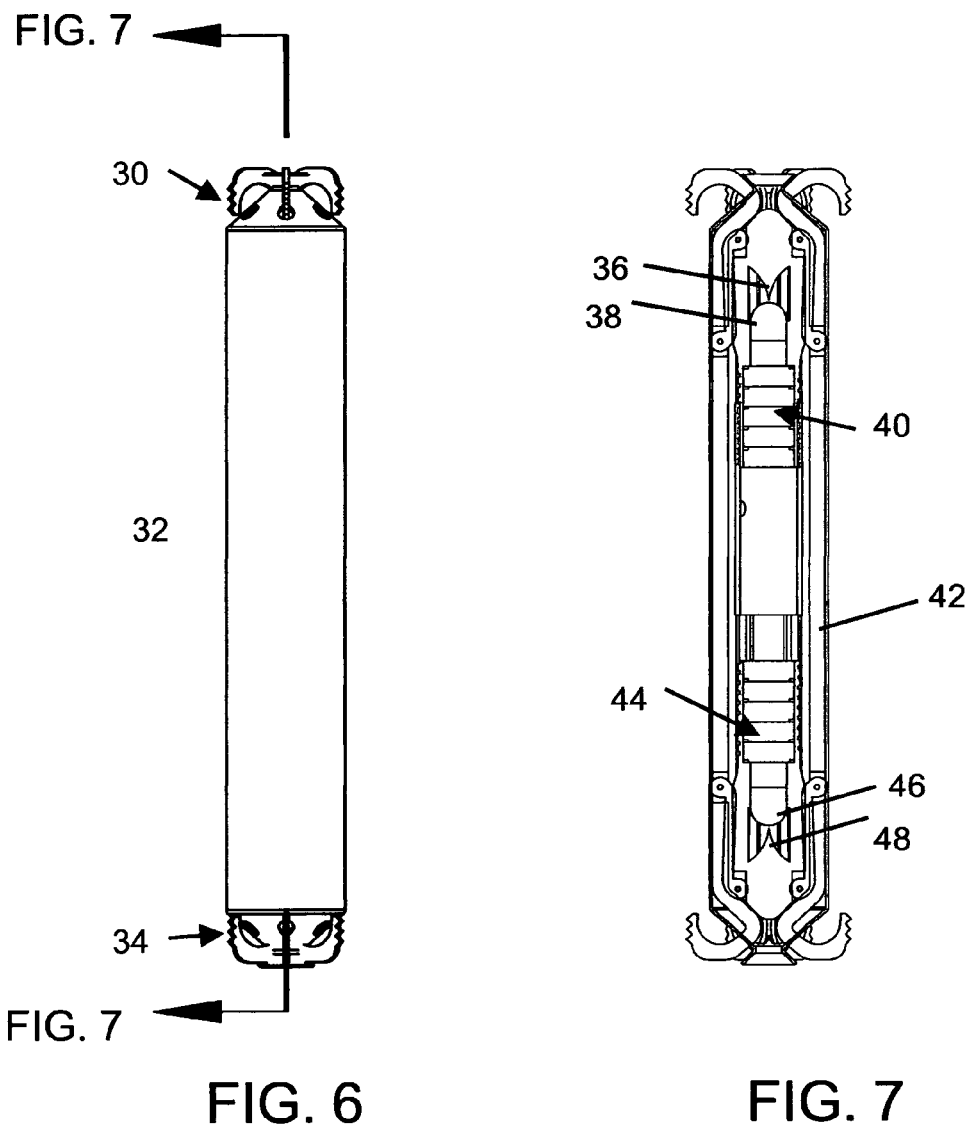

FIG. 6 depicts a side exterior view of an implantable embodiment of the invention in a collapsed state.

FIG. 7 depicts a side cross sectional view of an implantable embodiment of the invention in a collapsed state.

Figure 8:
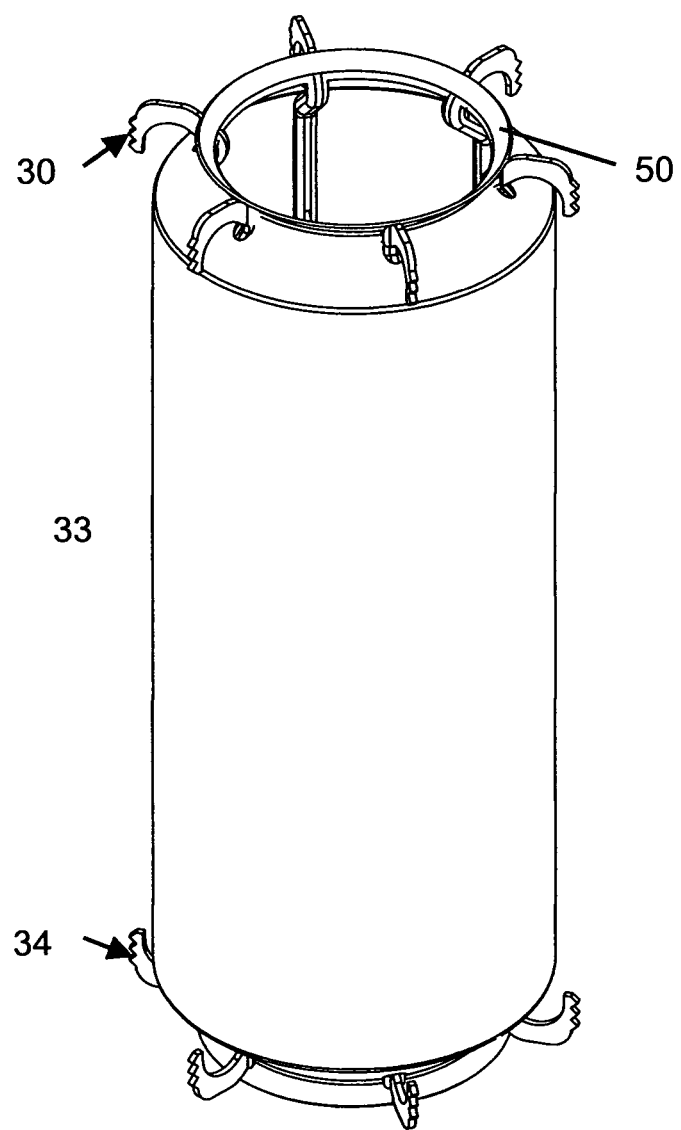

FIG. 8 depicts an off-axis exterior view of an implantable embodiment of the invention in an expanded state.

FIG. 9 depicts a side exterior view of an implantable embodiment of the invention in an expanded state.

FIG. 10 depicts a side cross sectional view of an implantable embodiment of the invention in an expanded state.

Figure 11:
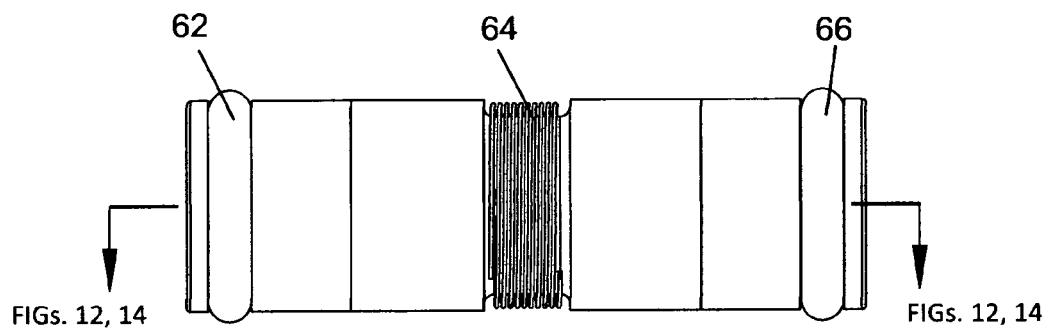

FIG. 11 depicts a side exterior view of an alternative embodiment of the invention.

Figure 12:
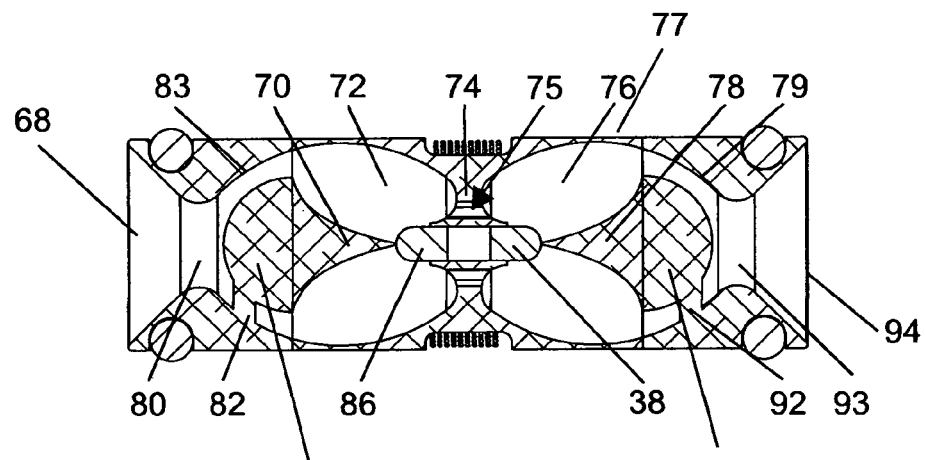

FIG. 12 depicts a side cross sectional view of an alternative embodiment of the invention.

Figure 13:
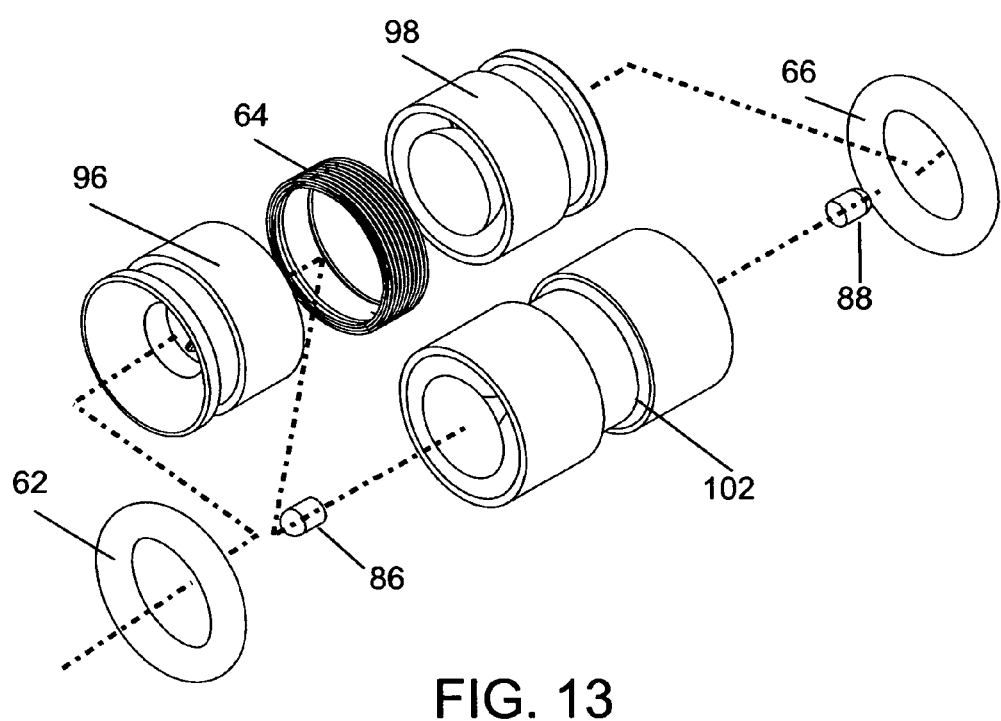

FIG. 13 depicts a blow apart view of an alternative embodiment of the invention.

Figure 14:
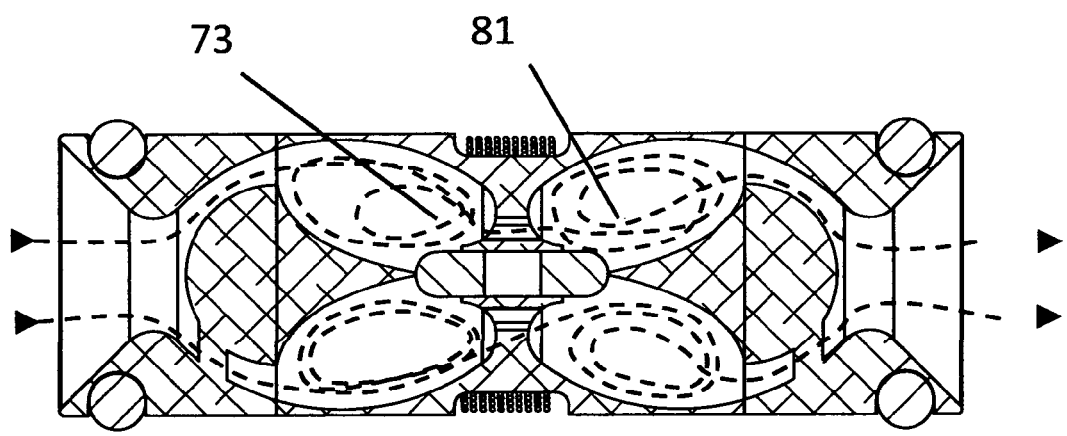

FIG. 14 depicts a side cross sectional view of an alternative embodiment of the invention with dashed curves to indicate flow paths.

Figure 15:
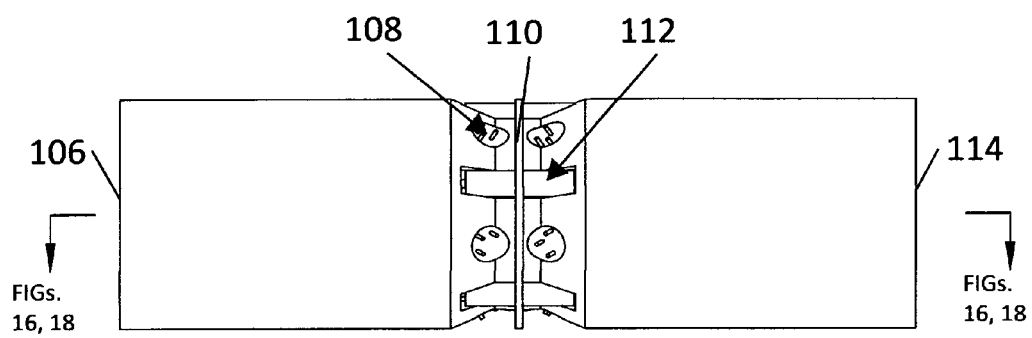

FIG. 15 depicts a side exterior view of a second alternative embodiment of the invention.

Figure 16:
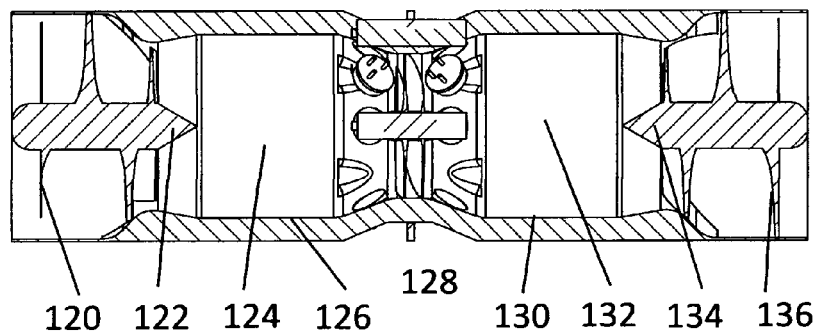

FIG. 16 depicts a side cross sectional view of a second alternative embodiment of the invention.

Figure 17:
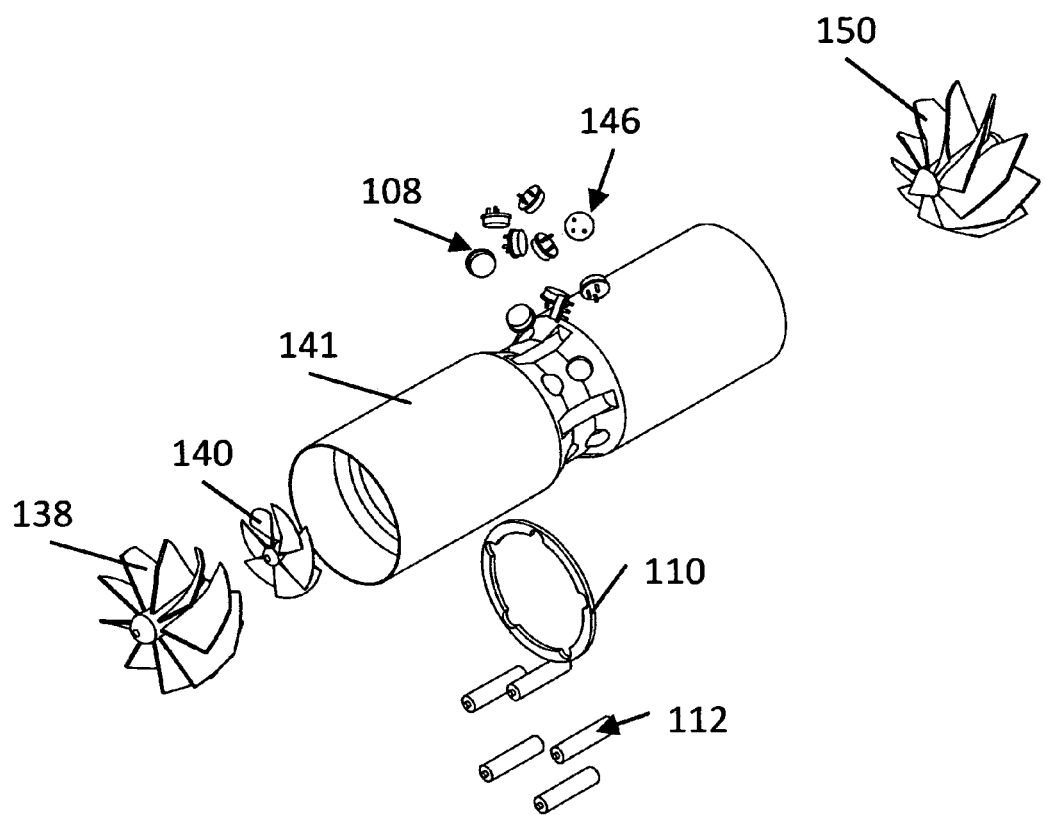

FIG. 17 depicts a blow apart view of a second alternative embodiment of the invention.

Figure 18:
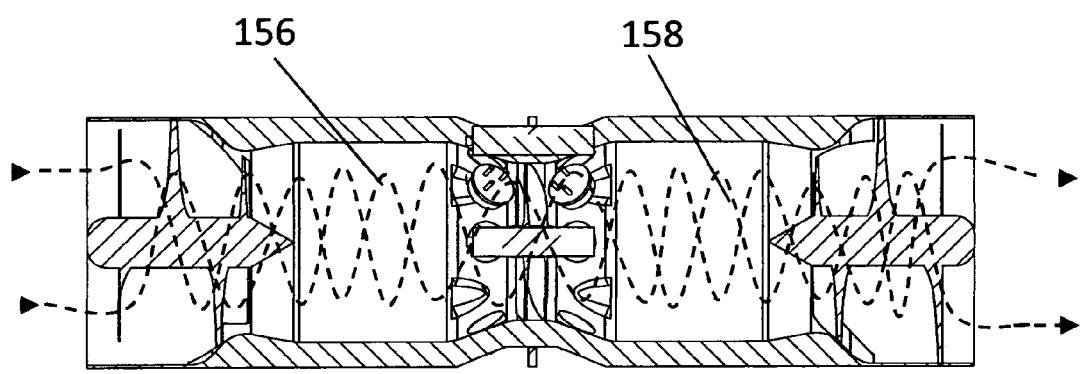

FIG. 18 depicts a side cross sectional view of a second alternative embodiment of the invention with dashed curves to indicate flow paths.

DETAILED DESCRIPTION

Reference will now be made to various embodiments of the apparatus for infection control, examples of which are illustrated in the accompanying drawings, wherein like numerals indicate the same element throughout views.

FIG. 2 depicts an embodiment of the apparatus for infection control. In this embodiment, an apparatus for infection control 14 is shown in a patient's trachea 12. The patient 10 is shown positioned for implantation. The device could also be located less or more deep in the tracheal path, including in the bronchi. The device could also be implanted into the nasal cavity to sterilize nasal air while allowing higher air flows through the mouth when needed. In this embodiment, the apparatus for infection control can sterilize both air inhaled by the patient and the air exhaled by the patient. Sterilization of exhalation may support the containment of contagious disease or other biological contaminants.

FIG. 3 depicts an apparatus for infection control 18 placed within a tracheal tube 20, between a patient 16 (schematically shown) and a ventilator system 22. While the apparatus for infection control 18 is shown at the distal end of the tracheal tube 20, it could also be located more proximally to the ventilator, as preferred. The device could also be located at the intake of the ventilator system in order to sterilize incoming air and contaminants prior to entering the system. Any embodiment described may be used within a ventilator system in a hospital or home setting.

FIG. 4 shows the apparatus for infection control 28 in blow apart relation to a gas mask or other device that constrains the breathing pathway to an opening 26. In practice, the apparatus for infection control 28 would be connected in an airtight manner to a mask 24 via airway opening 26. Thus, the apparatus for infection control could sterilize inhalations and exhalations of the wearer. The mask is not limited to fitting just one person. It could fit multiple people. It also could cover only the nose and mouth, just the mouth, or just the nose. Also, the mask may have multiple instances, various sizes, or both of an apparatus for infection control 28 attached to various airways to increase capacity.

Exemplary Embodiment

One embodiment of the apparatus for infection control (device) is shown in FIG. 5 (isometric view, collapsed configuration), 6 (side view, collapsed configuration), 7 (cross section, collapsed configuration), 8 (isometric view, expanded configuration), 9 (side view, expanded configuration), and 10 (cross section, expanded configuration). The device is shown in a collapsed configuration in FIGS. 5, 6, and 7 and an expanded configuration in FIGS. 8, 9, and 10. In this embodiment, anchoring elements 30, 34 are shown in FIGS. 5, 6, 8, and 9. The anchoring elements are integral to outer frame 53 shown in FIG. 10. The outer frame 53 connect to reflective caps 54, 60 via struts 52, 58 and a flexible UV containment shield 42. Preferably there are 6 struts 52, 58 at each end that expand the UV containment shield 42 evenly. The outer frames 53, struts 52, 58, reflective inlet cap 54, and reflective outlet cap 60 are connected via pivoting rivets 55 that allow single axis rotation at their joints. The outer frames 53 and struts 52, 58, are preferably made of polycarbonate or other tough, UV stable, non-bioreactive material, which may be UV absorbing or coated with a UV absorbing material. The pivoting rivets 55 preferably are made of aluminum or other tough, UV stable, malleable, non-bioreactive material or other appropriate material, which may be coated with a UV absorbing material. The UV containment shield 42 is made of mylar or other flexible, UV reflecting material. The reflective caps 54, 60 are preferably made of aluminum to reflect the UV light and dissipate excess heat from the UV LEDs. The reflective caps 54, 60 are connected by a central nut 56 where one cap has external left handed threads and the other cap has external right handed threads. The central nut 56 has one half internally left handed threads and half internally right handed threads to connect to the reflective caps 54, 60. Alternatively, the reflective caps 54, 60 and the central nut 56 may engage by a ratcheting mechanism. The mechanism would allow for expansion of the device diameter as the two reflective caps 54, 60 move toward each other and the central nut. The reflective caps 54, 60 and the central nut 56 contain a plurality of UV light sources 38, 46, batteries 40, 44, and necessary electrical connections (not specifically shown). One or more batteries can be used and are preferably composed of two sets of 5 lithium button batteries wired as 2 in series and 5 in parallel to create the 6V needed to drive the LEDs and the current to drive them for extended time.

One embodiment of the apparatus for infection control is depicted in FIG. 5, which illustrates a device that can be implanted as shown in FIG. 2. The device is implanted in a collapsed configuration 32 as depicted in FIGS. 5, 6, and 7. The device is composed of one or more batteries 40, 44 electrically connected to one or more UV light sources 38, 46. The UV light sources 38, 46 power may be controlled by a conventional flow activated switch (not shown) which applies power when flow is detected, by a conventional direct connect switch (not shown) activated when the nut 56 drives the reflective caps 54, 60 towards each other, or by a conventional external switch (not shown). Each light source is directed at a reflective surface 36, 48 which redirects the light emitted from a co-axial direction to a radial direction. The use of conical, hemispherical, and other shapes for the reflective surface 36, 48 could also create this redirection for the light. The reflective surface 36, 48 could be a polished aluminum surface or other UV reflective surface. The use of the reflective surface to create reflection of UV light in a radial direction increases the exposure of UV light to the fluid passing through. The use of the reflective surfaces also significantly reduces the chance of UV light escaping the device. Surrounding the batteries 40, 44, UV light sources 38, 46, and reflective surfaces of the device is a flexible UV containment shield 42 to protect the patient from UV exposure. A collapsible frame consisting of the outer frames 53 and struts 52, 58 connects the UV light sources 38, 46, batteries 40, 44, and reflective surfaces 36, 48 to the shield and allows for expansion and contraction of the lumen created within the apparatus. The reflective caps 54, 60 that hold the UV light sources 38, 46 and batteries 40, 44 connect from the struts at one end and thread into the central nut 56. The central nut 56 has one half internally left handed threads and half internally right handed threads. The reflective inlet cap 54 threads into the central nut from the inlet side. The reflective outlet cap 60 threads into the central nut 56 from the opposite side. Once the device is placed as desired by the physician or other user, the physician holds the device steady and rotates the nut 56 via a conventional tool such as a flexible torque driver (not shown). Rotation of the nut 56 against the reflective caps 54, 60 causes the reflective caps to move towards each other. This motion causes the struts 52, 58 to push against the UV containment shield 42. Because the outer frame 53 has a constant length, the strut motion causes the shield to expand, allowing for wall apposition within a lumen of appropriately similar diameter.

An expanded configuration 33 is depicted in FIGS. 8, 9, 10. The collapsible frame expands to conform to the diameter of the individual patients trachea or other appropriate area. Also, on the ends of the outer frame 53 are anchoring elements 30, 34 to resist migration once placed in the anatomy of the patient. The shield may have an inner lip 50 in order to reduce the escape of UV light from the device.

Additional Embodiments

Another embodiment of the device is shown in FIGS. 11 (side view, assembled), 12 (cross section, side view, assembled), 13 (isometric, exploded view), and 14 (cross section, side view, assembled, fluid flow lines).

This embodiment is composed of three major sections: an inlet section 96, sterilization section 102, and an outlet section 98. The inlet section 96 has an inlet 68, an inlet bulbous element 84 supported by multiple inlet struts 82, and an inlet exterior housing 80 which creates an inlet inner surface 83. The components of the inlet section 96 are made of UV absorbing material. One embodiment includes components manufactured by Acktar Ltd., preferably carbon filled polycarbonate with the interior surface inlet inner surface 83 coated in a UV absorbing material such as ULTRA BLACK® optical coating, carbon, avobenzone, octyl methoxycinnamate, benzophenone, or a roughened dark surface. The inlet section 96 is constructed preferably by molding the inlet 68 and the inlet exterior housing 80 as one part and inserting a second molded part consisting of the inlet bulbous element 84 and the inlet struts 82. The inlet struts 82 connect to the inlet exterior housing 80.

The outlet section 98 has an outlet 94, an outlet bulbous element 90 supported by multiple outlet struts 92, and an outlet exterior housing 93 which creates an outlet inner surface 79. The components of the outlet section 98 are made of UV absorbing material. One embodiment includes components made of carbon filled polycarbonate or other material with the outlet inner surface 79 coated in a UV absorbing material such as ULTRA BLACK® optical coating, carbon, avobenzone, octyl methoxycinnamate, benzophenone, or a roughened dark surface. The outlet section 98 is preferably constructed by molding the outlet 94 and the outlet exterior housing 93 as one part and inserting a second molded part consisting of the outlet bulbous element 90 and the outlet struts 92. The outlet struts 92 key into the outlet exterior housing 93.

The sterilization section 102 is made of a UV reflective material with good heat conduction, preferably but not limited to aluminum. The sterilization section 102 is composed of three segments, which are preferably constructed as three machined aluminum parts: Reflective cones 70, 78 and a central housing 77. The reflective cones 70, 78 are attached to the inlet and the outlet bulbous elements 84, 90 through various methods such as adhesive attachment, threaded attachment or other appropriate methods. The space surrounding the reflective cone 70 and within the sterilization section 102 creates the first sterilization chamber 72. The space surrounding the reflective cone 78 and the sterilization section 102 creates the second sterilization chamber 76. The central housing 77 may be machined into shape with one or more pass through channels 75 that are arranged preferentially in a radial pattern with the material between these channels forming central struts 74. The sterilization section also contains UV LEDs 86, 88, energizing coil 64, and conventional wiring (not shown). The UV LEDs 86, 88 are preferably Sensor Electronic Technology, Inc. (SETi) UVTOP260TO39BL LEDs which emit light in a range of 260-270 nm wavelength, have 300 uW optical power output for each LED, require 6.75V driving input, and emit at a 7 degree viewing angle. Viewing angle is defined as the total angular divergence of the light emitted. The UV LEDs 86, 88 are bonded into the central housing 77, preferably with thermally conductive epoxy in a back-to-back configuration. The energizing coil 64 is preferably composed of fifty coils of 28 awg copper core, epoxy insulated motor wire. The conventional wiring (not shown) consists of 28 awg PVC insulated wires to connect each of UV LEDs 86, 88 to the coil in parallel. The inlet section 96 and outlet section 98 are bonded via a suitable method such as adhesive or friction welding to the sterilization section 102. The exterior of the inlet and outlet sections 96, 98 also include a pair of o-rings 62, 66 made of compliant rubber.

The inlet 68 of the inlet section 96 allows fluid to pass into the sterilization section 102 while not allowing significant sterilizing light to escape out. It does this by channeling the fluid radially around the inlet bulbous element 84 that is maintained in the flow path by the inlet struts 82. The fluid passes the inlet bulbous element 84 along the inlet outer wall 83 and into a first sterilization chamber 72. In order to protect against the escape of significant sterilizing light, the inlet exterior housing 80 narrows in front of the bulbous element 84. Because of these elements and the non-UV-reflecting surfaces on the exterior housing 80 inner surface and the bulbous element 84, light does not have a path out of a first sterilization chamber 72 without being dissipated.

Within a first sterilization chamber 72, fluid is forced into a turbulent flow while the UV LED 86 emits UV light into the chamber. The turbulent flow causes the fluid and its contaminants to be exposed to the light emitted by the UV LED 86 multiple times and in multiple directions. The turbulent flow is created by the flow through the channels 75 adjacent the central struts 74, which support the UV LEDs 86, 88. The central struts 74 cause part of the flow to move through the channels 75 to a second sterilization chamber 76 and part of the flow to move in a retrograde direction within a first sterilization chamber 72. When this flow rejoins the fluid inflow, a vortex is formed creating an inlet turbulence 73. The central struts 74 have significant gaps between them to allow the fluid flow to proceed into a second sterilization chamber 76. Within the first sterilization chamber 72, the UV LED 86 is directed at the UV reflective surface of the reflective inlet cone 70. This surface redirects the majority of the UV light from a co-axial direction to a radial direction ensuring that the entire fluid flow is exposed to the emitted UV light. The interior surface of the sterilization section 102 is highly UV reflective so the light is reflected multiple times across the chamber further increasing the exposure of the fluid flow to UV light.

The sterilization section 102 contains the power and control system on the outside of the central housing 77. The energizing coil 64 is energized by a magnetic field created by the alternating current flowing through an electrical wire coil external to the respiratory tube (not shown). The driven coil has an alternating current flowing in it driven by induction from the external wire coil A conventional rectifier (not shown) converts the driven coil's current into DC current which is then used to drive the LEDs. Current is conducted to the UV LEDs 86, 88 through wires within the central struts 74. The central struts 74 also act as a heatsink for the UV LEDs 86, 88 by transferring generated heat to the fluid flow and the adjacent material.

A second sterilization chamber 76 contains another UV LED 88 directed towards the UV reflective surface of the outlet reflective cone 78, which redirects the UV light from co-axial to radial. The chamber is also designed to cause fluid flow tore-circulate creating an outlet turbulence 81, exposing the fluid and its contaminants to the UV light multiple times. The interior surface of a second sterilization chamber 76 is preferably reflective to UV light in order to increase the fluid exposure to the UV light.

At the distal end of the chamber there is the outlet section 98 with an inlet that is not aligned with the centerline of the device or the channels 75. This causes the fluid to follow the parabolic path of outlet reflective cone 78 thus causing further turbulence 81. The outlet section 98 interior surfaces are coated with or made of UV absorbing material. The fluid flow path tapers toward the centerline around the outlet bulbous element 90 which is supported by the outlet struts 92 and continues along the path of the outlet inner surface 79 such that the UV light cannot escape without hitting the UV absorbent surfaces of the outlet section 98. The fluid flow then exits via the outlet 94.

Exterior to the entire assembly are the two compliant O-rings 62, 66 which seal the device to the interior surface of the fluid tube in which it may be installed.

Another embodiment of the device is shown in FIGS. 15 (side view, assembled), 16 (cross section, side view, assembled), 17 (isometric, exploded view), and 18 (cross section, side view, assembled, fluid flow lines)

This embodiment consists of an exterior casing 141, an inlet blade assembly 138, a middle section 128, and an outlet blade assembly 150. The exterior casing 141 consists of an inlet 106, a chamber surface 126 which creates a sterilization chamber 124, the middle section 128, a chamber surface 130 which creates a second sterilization chamber 132, and finally an outlet 114. The exterior casing 141 is preferably made of aluminum for its UV reflectivity and thermal conduction. The exterior casing 141 is made by machining an aluminum casting or other appropriate techniques to create the interior surfaces and electronic mount points in the middle section 128. The inlet blade assembly 138 consists of inlet blades 120 preferably with multiple blades and preferably molded from UV absorbing carbon filled polycarbonate (nine blades are shown). The inlet blades 120 are keyed into an UV reflective hub 122 which can be constructed of aluminum or other materials sufficiently capable of efficiently reflecting light in the UV spectrum. At the middle section 128, slots or other recesses are provided for two sets of UV LEDs 108, 146 (ten UV LEDs are shown) and also holds an appropriate number of batteries 112 to power the UV LEDs (five AAA batteries are shown), which are connected to the UV LEDs 108, 146 by a parallel wiring of conventional 28 AWG wires (not shown). The UV LEDs 108, 146 are preferably Sensor Electronic Technology Inc (SETi) UVTOP260TO39BL LEDs which have a range of 260-270 nm wavelength, 300 uW optical power output, 6.75V driving input, and 7 degree viewing angle. The batteries 112 are preferably based on lithium polymer chemistry and are connected in a parallel configuration. The batteries 112 are secured with a ring clip 110 preferably made of a compliant rubber material. Also, within the middle section, a tertiary blade assembly 140 is bonded. The tertiary blade assembly 140 is constructed from aluminum for UV reflectivity and thermal conductivity. The outlet blade assembly 150 consists of outlet blades 136, preferably with multiple blades and preferably molded from UV absorbing carbon filled polycarbonate (nine blades are shown). The outlet blades 136 are keyed into a reflective hub 134, preferably constructed of aluminum. The inlet blade assembly 138 and the outlet blade assembly 150 are bonded to the exterior casing 141 at the outer edges of the blades to complete the assembly.

The inlet 106 allows fluid to enter the device and begin to follow a helical flow path 156. The inlet section is composed of the inlet blades 120 that drive the fluid into the helical path 156 while not significantly increasing the device's flow resistance. The blades have UV absorbent surfaces so as to contain the UV light inside the device. By choosing an appropriate number of blades for a given blade pitch, the inlet blade assembly 138 is constructed so that there is no straight path such that the amount of UV light that can escape the UV exposure chamber is reduced. Furthermore, the pitch of the blades is preferably increasing so that the fluid is further spun in the helical path 156.

Within the sterilization chamber 124, the fluid is forced into the turbulent flow 156 while the UV LEDs 108 emit UV light into the chamber. Turbulent flow causes the fluid and its contaminants to be exposed to the light emitted from the UV LEDs 108 multiple times and in multiple directions. The UV LEDs 108 are positioned around the circumference of the sterilization chamber 124, and directed into the chamber toward the main axis at an angle to the orthogonal of the main axis. The chamber surface 126 is UV reflective. The slight angle causes the UV light to be repeatedly reflected across the chamber as it progresses towards the inlet chamber. This reflection continues until the majority of the UV light strikes the reflective hub 122 which reverses the progression back, away from the inlet 106. These repeated reflections increase the probability that any fluid contaminants are significantly exposed to UV light in many directions.

Fluid flow then reaches the middle section 128 where the tertiary blade assembly 140 helps to continue the helical fluid flow 156 and to dissipate waste heat generated from the UV LEDs 108 to the fluid flow. Shown are five UV LEDs 108 directed into the first sterilization chamber, toward the inlet. Five more LEDs 146 are oriented toward the second sterilization chamber 132 and the outlet 114. Alternatively, a different quantity of LEDs could be directed into each chamber, depending on UV output requirements, power requirements, and other factors such as medium to be sterilized and flow rate of the medium. Between the LEDs, the batteries 112 (appropriate quantity of batteries would be dependent on the requirements of the LEDs employed) are located to supply power for the LEDs. The batteries are secured with the ring clip 110.

The fluid then flows from the middle section 128 to the second sterilization chamber 132. The second sterilization chamber 132 and the outlet 114 is effectively a mirror of the first sterilization chamber 124 and the inlet 106. The second sterilization chamber 132 is enclosed by the chamber surface 130, which is UV reflective. The light from the UV LEDs 146 is directed into the chamber toward the main axis at an angle to the orthogonal of the main axis such that the UV light repeatedly crosses the chamber and reflects until it strikes the reversing reflective cone 134 which causes the light to reflect repeatedly back towards the middle section 128. The fluid flow continues through the chamber in a helical path 158. The UV light is contained within the second chamber by the outlet blade assembly 150, which relies on the outlet blades 136, particularly their shape and absorbency to reduce any UV light directed toward the outlet 114 from escaping.

The reader will see that at least one embodiment of the apparatus for infection control allows for it to be located or placed in areas that are space constrained, including intraluminal placement through careful selection of light sources and placement of those sources and possible use of a flexible or collapsible design. Similarly, at least one embodiment includes designs to provide high infection control efficiency through use of turbulence-creating fluid handling and/or use of designs that make effective use of light through multiple reflections while trapping the light from escaping, which could cause harm. Finally, the reader can see that at least one embodiment can physically isolate the material flowing within the lumen from the exterior of the device by use of an electromagnetic field to provide power to interluminal light source(s), which can substantially reduce the risk of external contamination by the internal material and also provide for easier methods of manufacturing.

The description above provides several specifications but these should not be construed as limiting, unless explicitly indicated. The specifications are intended to be examples of embodiments. Of course, many other variations are possible.

For example, there are various ways of creating turbulence. This could include the use of mesh in multiple orientations or luminal dividers. The mechanism to create turbulence could be static or in motion. Textures on the surface of the lumens could also be used to create turbulence. A venturi nozzle, or other method of speeding up or slowing down the fluid flow, could also create turbulence.

Additionally, there are various methods of creating UV light. The UV light could be from UV arc lamps, UV laser, UV incandescent lamps, or fluorescent chemical reaction. The light source could be extraluminal, the lumen itself, or transfer optically from an external source.

There are also various ways of creating the sterilizing action. The sterilizing action could come from electrostatic discharge, chemical reaction, infrared radiation, heat or ozone.

For example, there are numerous ways to contain the UV light. The UV light could be contained using UV absorbing tortuous paths, reflective tortuous paths, radial vanes, parallel vanes, meshes, woven clothes, knitted clothes, random fiber meshes, dual orthogonal polarizing filters, flow driven flap covers, active flap covers, or radial flaps.

For example, there are numerous ways the UV light source could be powered. The light source could be powered by batteries, turbine driven by fluid flow, external magnetic field, external DC power, external AC power, external light, and external heat. The apparatus for infection control could also reduce power usage by flashing or pulsing its output or varying output as the flow rate requires.

For example, there are numerous possible applications of the apparatus for infection control. The apparatus for infection control is applicable to any need for containment or exclusion of biological materials or any materials affected by UV radiation. These applications include keeping contagious disease from spreading from a patient with disease, sterilizing volumes of air in a building or room, sterilizing air in aircraft, sterilizing air in automobiles, sterilizing fluids, sterilizing vacuum airflow, sterilizing alcohol post fermentation, sterilizing airflow within an AC unit, sterilizing airflow in a CPAP system, and personal protection on aircraft.

As such, the claims (and their equivalents) should be the basis of the scope, not the disclosed embodiments.

The invention claimed is:

1. A sterilization device comprising:
   a proximal end;
   a distal end;
   a lumen extending between the proximal end and the distal end, wherein the lumen is configured to allow the passage of fluid between the proximal end and the distal end; and
   a light source wherein the light source is configured to emit light into the lumen between the proximal end and the distal end and wherein the light source is located within the lumen cavity and wherein the light source is configured to emit a frequency and intensity of light sufficient to sterilize material flowing through the lumen.

2. The sterilization device of claim 1, further comprising a power storage device located within the lumen, wherein the power storage device is configured to provide power to the light source.

3. The sterilization device of claim 1, further comprising an inner magnetic coil, wherein upon an outer magnetic coil being placed in proximity to the inner magnetic coil, the inner magnet coil and the outer magnetic coil are configured to generate an electromagnetic field that is configured to provide power to the light source.

4. The sterilization device of claim 1, wherein the light source comprises at least one LED.

5. The sterilization device of claim 4, wherein the light source is configured to emit light in the range of 200 nm to 280 nm.

6. The sterilization device of claim 1, further comprising a first light trap at the proximal end and a second light trap at the distal end, wherein at least one of the light traps allows fluid flow while reducing the light allowed to pass.

7. The sterilization device of claim 1, wherein a surface of the device comprises a reflective substance, wherein the reflective substance is configured to reflect at least some of the light emitted by the light source, and these reflection cause the fluid to be exposed to the light via a non-direct path from the source.

8. The sterilization device of claim 1, wherein the device disipates heat to the flowing fluid.

9. The sterilization device of claim 1, wherein the device, including light source, is located within the trachea.

10. A sterilization device comprising:
    a proximal end,
    a distal end, and
    a lumen extending between the proximal end and the distal end wherein the lumen is configured to allow the passage of fluid between the proximal end and the distal end;
    a light trap, wherein the light trap allows significant fluid flow while reducing the light allowed to pass and is formed of a material that is not permeable to fluid; and
    an airflow handler configured to cause a turbulent flow of material passing between the proximal end and the distal end.

11. The sterilization device of claim 10, further comprising a light source, located within the lumen cavity, wherein the light source is configured to emit light into the lumen between the proximal end and the distal end and wherein the light source is configured to emit a frequency and intensity of light sufficient to sterilize material passing through the lumen.

12. The sterilization device of claim 10, wherein the light source is configured to emit light in the range of 200 nm to 280 nm.

13. The sterilization device of claim 10, wherein the device disipates heat to the flowing fluid.

14. The sterilization device of claim 10, wherein a surface of the device comprises a reflective substance, wherein the reflective substance is configured to reflect at least some of the light emitted by the light source.

15. A sterilization device comprising:
    a proximal end;
    a distal end;
    a lumen extending between the proximal end and the distal end, wherein the lumen is configured to allow the passage of fluid between the proximal end and the distal end; wherein a portion of said lumen can expand radially from a collapsed configuration to a plurality of expanded configurations; and
    a light source, configured to emit light into the lumen between the proximal end and the distal end, wherein the light source is configured to emit a frequency and intensity of light sufficient to sterilize material passing through the lumen.

16. The sterilization device of claim 15, wherein the light source is located within the lumen cavity.

17. The sterilization device of claim 15, further comprising a power storage device located within the lumen, wherein the power storage device is configured to provide power to the light source.

18. The sterilization device of claim 15, wherein the light source comprises at least one LED.

19. The sterilization device of claim 16, wherein the light source is configured to emit light in the range of 200 nm to 280 nm and wherein the device disipates heat to the flowing fluid.

20. The sterilization device of claim 15, further comprising a first light trap at the proximal end and a second light trap at the distal end, wherein at least one trap allows fluid flow while reducing the light allowed to pass and is formed of a material that is not permeable to fluid.

\* \* \* \* \*